(12) United States Patent
Hayashi et al.

(10) Patent No.: US 12,111,256 B2
(45) Date of Patent: Oct. 8, 2024

(54) BIOLOGICAL COMPONENT MEASUREMENT APPARATUS

(71) Applicant: Mitsubishi Electric Corporation, Tokyo (JP)

(72) Inventors: Shusaku Hayashi, Tokyo (JP); Koichi Akiyama, Tokyo (JP); Yuki Tsuda, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 200 days.

(21) Appl. No.: 17/772,527

(22) PCT Filed: Jul. 27, 2020

(86) PCT No.: PCT/JP2020/028648
§ 371 (c)(1),
(2) Date: Apr. 28, 2022

(87) PCT Pub. No.: WO2021/131126
PCT Pub. Date: Jul. 1, 2021

(65) Prior Publication Data
US 2022/0404275 A1 Dec. 22, 2022

(30) Foreign Application Priority Data
Dec. 23, 2019 (JP) .................. 2019-231088

(51) Int. Cl.
*G01N 21/41* (2006.01)
*A61B 5/1455* (2006.01)
(52) U.S. Cl.
CPC ........... *G01N 21/41* (2013.01); *A61B 5/1455* (2013.01)

(58) Field of Classification Search
CPC ................. G01N 21/41; G01N 21/552; G01N 2021/1712; G01N 21/171; A61B 5/1455
See application file for complete search history.

(56) References Cited

U.S. PATENT DOCUMENTS

2006/0074281 A1* 4/2006 Hwang ............... A61B 5/1455
600/310
2011/0024630 A1 2/2011 Sundaram et al.
(Continued)

FOREIGN PATENT DOCUMENTS

JP 2005334281 A * 12/2005
JP 2007-301154 A 11/2007
(Continued)

OTHER PUBLICATIONS

English Translation of Maruo et al. JP2005334281A Description (Year: 2005).*
(Continued)

*Primary Examiner* — Tarifur R Chowdhury
*Assistant Examiner* — Akbar H. Rizvi
(74) *Attorney, Agent, or Firm* — XSENSUS LLP (57) ABSTRACT

A biological component measurement apparatus includes an optical medium, an excitation light source, a probe light source, and a light position detector. The optical medium includes a sample placement surface. The excitation light source emits excitation light toward a sample placed on the sample placement surface. The probe light source emits probe light that travels through the optical medium. The light position detector detects the position of the probe light outgoing from the optical medium. The optical medium is formed from chalcogenide glass.

12 Claims, 5 Drawing Sheets

(56) References Cited

U.S. PATENT DOCUMENTS

| | | | |
|---|---|---|---|
| 2017/0082538 A1* | 3/2017 | Hoke | G01N 21/552 |
| 2017/0146455 A1* | 5/2017 | Mäntele | G01N 21/636 |
| 2018/0306726 A1 | 10/2018 | Mannhardt et al. | |
| 2018/0328835 A1* | 11/2018 | Bauer | G01N 21/171 |
| 2018/0337165 A1 | 11/2018 | Migita | |

FOREIGN PATENT DOCUMENTS

| | | | |
|---|---|---|---|
| JP | 2017-519214 A | 7/2017 | |
| JP | 2018-194423 A | 12/2018 | |
| JP | 2019-507319 A | 3/2019 | |
| WO | WO-2019150543 A1 * | 8/2019 | A61B 5/1455 |

OTHER PUBLICATIONS

English Translation of Akiyama et al. WO2019150543A1 Description (Year: 2019).*

Indian Office Action issued Sep. 22, 2022, in Indian Application No. 202227033124.

International Search Report mailed on Oct. 13, 2020, received for PCT Application PCT/JP2020/028648, Filed on Jul. 27, 2020, 12 pages including English Translation.

Notice of Reasons for Refusal mailed on Apr. 13, 2021, received for Japanese Application No. 2021-500479, 12 pages including English Translation.

Decision of Refusal mailed on Aug. 31, 2021, received for Japanese Application No. 2021-500479, 6 pages including English Translation.

* cited by examiner

BIOLOGICAL COMPONENT MEASUREMENT APPARATUS

CROSS-REFERENCE TO RELATED APPLICATIONS

The present application is based on PCT filing PCT/JP2020/028648, filed Jul. 27, 2020, which claims priority to JP 2019-231088, filed Dec. 23, 2019, the entire contents of each are incorporated herein by reference.

TECHNICAL FIELD

The present disclosure relates to a biological component measurement apparatus.

BACKGROUND ART

National Patent Publication No. 2017-519214 (PTL 1) discloses a noninvasive analysis system including an optical medium, an infrared light source, a probe light source, and a photodiode. Specifically, a biological sample is placed on a surface of the optical medium. The infrared light source emits infrared light. The infrared light travels through the optical medium to illuminate the biological sample. The infrared light is absorbed by the biological sample to cause the biological sample to generate heat. The amount of absorption heat of the biological sample varies in a manner that depends on the amount or concentration of a biological component present in the sample or on the surface of the sample.

The probe light source emits, toward the optical medium, probe light that is visible light. The probe light is totally internally reflected at an interface between the optical medium and the biological sample to outgo from the optical medium. The absorption heat of the biological sample transfers to the optical medium to change a refractive index of the optical medium. The change in refractive index of the optical medium affects total internal reflection of the probe light at the interface between the optical medium and the biological sample to change a traveling direction of the probe light that outgoes from the optical medium. The photodiode detects a change in the traveling direction of the probe light. The amount or concentration of a biological component is measured based on the change in the traveling direction of the probe light detected by the photodiode. For example, when the sample is a skin of a patient, a blood glucose level of the patient is measured as a biological component.

CITATION LIST

Patent Literature

PTL 1: National Patent Publication No. 2017-519214

SUMMARY OF INVENTION

Technical Problem

In the noninvasive analysis system disclosed in PTL 1, however, the optical medium is formed from zinc sulfide (ZnS). Zinc sulfide (ZnS) has a high thermal conductivity of 27.2 W/(m·K). The absorption heat of the biological sample transfers to the optical medium and rapidly diffuses into the optical medium. This makes a change in refractive index of a part of the optical medium located on an optical path of the probe light smaller. This prevents the biological component from being measured with high accuracy. The present disclosure has been made in view of the above-described problems, and it is therefore an object of the present disclosure to provide a biological component measurement apparatus capable of measuring a biological component with improved accuracy.

Solution to Problem

A biological component measurement apparatus according to a first aspect of the present disclosure includes an optical medium, an excitation light source, a probe light source, and a light position detector. The optical medium includes a sample placement surface. The excitation light source emits, toward the sample placed on the sample placement surface, excitation light that travels through the optical medium. The probe light source emits probe light that travels through the optical medium. The light position detector detects a position of the probe light outgoing from the optical medium. In plan view of the sample placement surface, an optical path of the probe light in the optical medium overlaps a part of the sample placement surface irradiated with the excitation light. The optical medium is formed from chalcogenide glass.

A biological component measurement apparatus according to a second aspect of the present disclosure includes an optical medium, an excitation light source, a probe light source, and a light position detector. The optical medium includes a sample placement surface. The excitation light source emits, toward the sample placed on the sample placement surface, excitation light that travels through the optical medium. The probe light source emits probe light that travels through the optical medium. The light position detector detects a position of the probe light outgoing from the optical medium. In plan view of the sample placement surface, an optical path of the probe light in the optical medium overlaps a part of the sample placement surface irradiated with the excitation light. The optical medium is formed from a material having a thermal conductivity of less than or equal to 15.0 W/(m·K).

Advantageous Effects of Invention

In the biological component measurement apparatus according to the first aspect of the present disclosure, the optical medium is formed from chalcogenide glass. In the biological component measurement apparatus according to the second aspect of the present disclosure, the optical medium is formed from a material having a thermal conductivity of less than or equal to 15.0 W/(m·K). In the biological component measurement apparatuses according to the first and second aspects of the present disclosure, the thermal conductivity of the material of the optical medium is less than the thermal conductivity (27.2 W/(m·K)) of zinc sulfide (ZnS). Therefore, a transfer of absorption heat of the sample makes a change in refractive index of a refractive index gradient region formed in the optical medium larger. This enables the biological component measurement apparatuses according to the first and second aspects of the present disclosure to measure a biological component with improved accuracy.

DESCRIPTION OF EMBODIMENTS

Hereinafter, embodiments will be described. Note that the same components are denoted by the same reference numerals to avoid the description from being redundant.

First Embodiment

Figure 1:
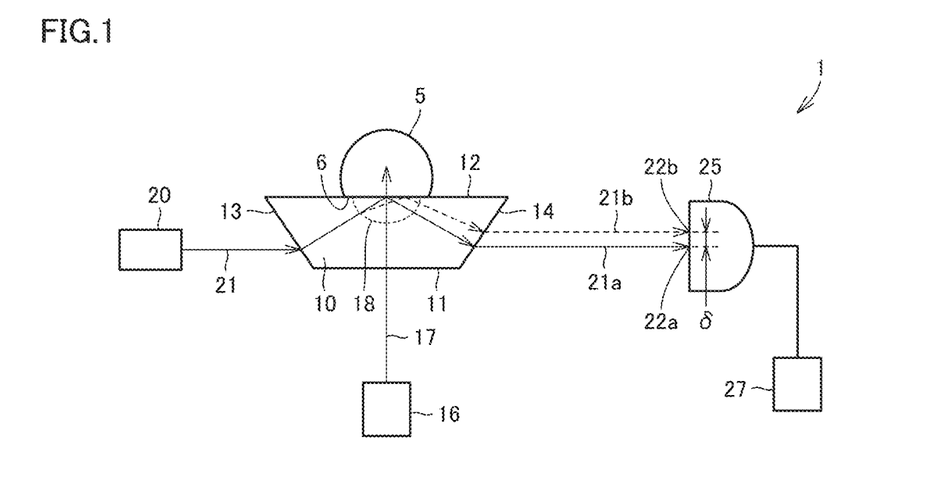
FIG. 1 is a diagram schematically illustrating a biological component measurement apparatus according to a first embodiment.

With reference to FIG. 1, a biological component measurement apparatus 1 according to a first embodiment will be described. Biological component measurement apparatus 1 mainly includes an optical medium 10, an excitation light source 16, a probe light source 20, a light position detector 25, and a biological component acquisition unit 27.

Optical medium 10 includes a first surface 11, a second surface 12 located on the opposite side of optical medium 10 from first surface 11, a third surface 13 connecting first surface 11 and second surface 12, and a fourth surface 14 connecting first surface 11 and second surface 12 and located on the opposite side of optical medium 10 from third surface 13. First surface 11 of optical medium 10 is a surface on which excitation light 17 emitted from excitation light source 16 impinges. Second surface 12 is a sample placement surface. A sample 5 is placed on second surface 12 and is in contact with second surface 12. Sample 5 is, for example, a skin or a body fluid of a patient. When a liquid is to be measured, sample 5 is a liquid contained in a transparent sample holder. Third surface 13 is a surface on which probe light 21 emitted from probe light source 20 impinges. A normal direction of third surface 13 is inclined from an incident direction of probe light 21. Fourth surface 14 is a surface from which probe light 21 outgoes. Fourth surface 14 is inclined from an outgoing direction of probe light 21. Optical medium 10 may be, for example, a total internal reflection prism (TIR prism).

Optical medium 10 is transparent to excitation light 17. Herein, the fact that optical medium 10 is transparent to excitation light 17 means that light transmittance of optical medium 10 with respect to excitation light 17 is greater than or equal to 25%. The light transmittance of optical medium 10 with respect to excitation light 17 may be greater than or equal to 50%, greater than or equal to 75%, or greater than or equal to 90%. Optical medium 10 is transparent to probe light 21. Herein, the fact that optical medium 10 is transparent to probe light 21 means that light transmittance of optical medium 10 with respect to probe light 21 is greater than or equal to 25%. The light transmittance of optical medium 10 with respect to probe light 21 may be greater than or equal to 50%, greater than or equal to 75%, or greater than or equal to 90%.

Optical medium 10 is formed from a material having a thermal conductivity of less than or equal to 15.0 W/(m·K). The thermal conductivity of the material of optical medium 10 may be less than or equal to 10.0 W/(m·K), less than or equal to 5.0 W/(m·K), less than or equal to 3.0 W/(m·K), less than or equal to 2.0 W/(m·K), or less than or equal to 1.0 W/(m·K). The thermal conductivity of the material of optical medium 10 is greater than or equal to 0.5 times a thermal conductivity of sample 5. The thermal conductivity of the material of optical medium 10 may be greater than or equal to 0.75 times the thermal conductivity of sample 5, may be greater than or equal to the thermal conductivity of sample 5, may be greater than or equal to 1.5 times the thermal conductivity of sample 5, or may be greater than or equal to 2.0 times the thermal conductivity of sample 5.

Optical medium 10 is formed from chalcogenide glass. For example, the chalcogenide glass contains 2 mol % to 22 mol %, both inclusive, of germanium (Ge), 6 mol % to 34 mol %, both inclusive, of at least one element selected from the group consisting of antimony (Sb) and bismuth (Bi), 1 mol % to 20 mol %, both inclusive, of tin (Sn), and 58 mol % to 70 mol %, both inclusive, of at least one element selected from the group consisting of sulfur (S), selenium (Se), and tellurium (Te). The chalcogenide glass has a thermal conductivity of 0.36 W/(m·K).

Excitation light source 16 emits excitation light 17 toward sample 5 placed on the sample placement surface (second surface 12). Excitation light 17 is emitted from excitation light source 16 to impinge on optical medium 10 through first surface 11. Excitation light 17 travels through optical medium 10. Excitation light 17 impinges on sample 5 through second surface 12. Excitation light 17 is absorbed by a biological component present in sample 5 or on a surface 6 of sample 5. For example, when the blood glucose level of the patient is measured using biological component measurement apparatus 1, the biological component is glucose present in interstitial fluid in epidermis. Excitation light 17 is absorbed by the biological component to generate absorption heat in sample 5. The absorption heat of sample 5 transfers to optical medium 10. A temperature gradient region is generated in optical medium 10, and a refractive index gradient region 18 is generated in optical medium 10 accordingly.

A wavelength of excitation light 17 is determined in accordance with an absorption wavelength of the biological component present in sample 5 or on surface 6 of sample 5. The wavelength of excitation light 17 may be longer than a wavelength of probe light 21. The wavelength of excitation light 17 is, for example, greater than or equal to 6.0 μm. The wavelength of excitation light 17 may be greater than or equal to 8.0 μm. The wavelength of excitation light 17 is, for example, less than or equal to 13.0 μm. The wavelength of excitation light 17 may be less than or equal to 11.0 μm. Excitation light 17 may be light having a plurality of wavelengths. For example, when the blood glucose level of the patient is measured using biological component measurement apparatus 1, the wavelength of excitation light 17 falls within a wavelength range including a wavelength of a fingerprint spectrum of glucose (for example, a wavelength range of greater than or equal to 8.5 μm to less than or equal to 10 μm). Excitation light source 16 is, for example, a quantum cascade laser capable of emitting broadband infrared light. Sample 5 may be irradiated with reference light that is not absorbed by the biological component present in sample 5 or on surface 6 of sample 5, together with excitation light 17.

Probe light source 20 emits probe light 21. Probe light 21 impinges on optical medium 10 through third surface 13 of optical medium 10. Probe light 21 is refracted by third surface 13 and travels through optical medium 10 toward the interface between optical medium 10 (second surface 12) and sample 5. In plan view of the sample placement surface (second surface 12), an optical path of probe light 21 in optical medium 10 overlaps a part of the sample placement surface (second surface 12) irradiated with excitation light 17. Probe light 21 is totally internally reflected at the interface between optical medium 10 (second surface 12) and sample 5. While probe light 21 is traveling through optical medium 10, probe light 21 travels through refractive index gradient region 18 generated in optical medium 10 by the absorption heat of sample 5. Probe light 21 is refracted by refractive index gradient region 18, and a traveling direction of probe light 21 changes accordingly. Probe light 21 (first outgoing probe light 21a and second outgoing probe light 21b) outgoes from fourth surface 14 of optical medium 10.

The wavelength of probe light 21 is, for example, greater than or equal to 1100 nm. The wavelength of probe light 21 may be greater than or equal to 1300 nm. The wavelength of probe light 21 is, for example, less than or equal to 1700 nm. Therefore, as the light source of probe light 21, an inexpensive semiconductor laser for use in optical communication such as an InGaAsP-based semiconductor laser or an InGaNAs-based semiconductor laser may be used. Further, probe light 21 is not visible light, so that it is possible to reduce the risk of damage to human eyes caused by probe light 21. The output of probe light 21 is, for example, less than or equal to 5 mW. This makes it possible to reduce the risk of damage to human eyes caused by probe light 21.

Light position detector 25 detects a position of probe light 21 (first outgoing probe light 21a and second outgoing probe light 21b) outgoing from optical medium 10. Light position detector 25 detects a first position 22a of probe light 21 (first outgoing probe light 21a) when sample 5 is not irradiated with excitation light 17. First position 22a of probe light 21 (first outgoing probe light 21a) is a position of probe light 21 (first outgoing probe light 21a) detected by light position detector 25 when sample 5 is not irradiated with excitation light 17. Light position detector 25 detects a second position 22b of probe light 21 (second outgoing probe light 21b) when sample 5 is irradiated with excitation light 17. Second position 22b of probe light 21 (second outgoing probe light 21b) is a position of probe light 21 (second outgoing probe light 21b) detected by light position detector 25 when sample 5 is irradiated with excitation light 17. Irradiating sample 5 with excitation light 17 causes the position of probe light 21 detected by light position detector 25 to shift from first position 22a to second position 22b.

Light position detector 25 outputs first position 22a of probe light 21 (first outgoing probe light 21a) and second position 22b of probe light 21 (second outgoing probe light 21b) to biological component acquisition unit 27. Light position detector 25 is, for example, a photodiode or a semiconductor position detection element.

Biological component acquisition unit 27 is connected to light position detector 25. Biological component acquisition unit 27 calculates a displacement amount δ of probe light 21, which is a distance between first position 22a and second position 22b to obtain the amount or concentration of the biological component present in sample 5 or on surface 6 of sample 5 based on displacement amount δ of probe light 21. Biological component acquisition unit 27 is, for example, one of the functions implemented by a processing unit.

Figure 2:
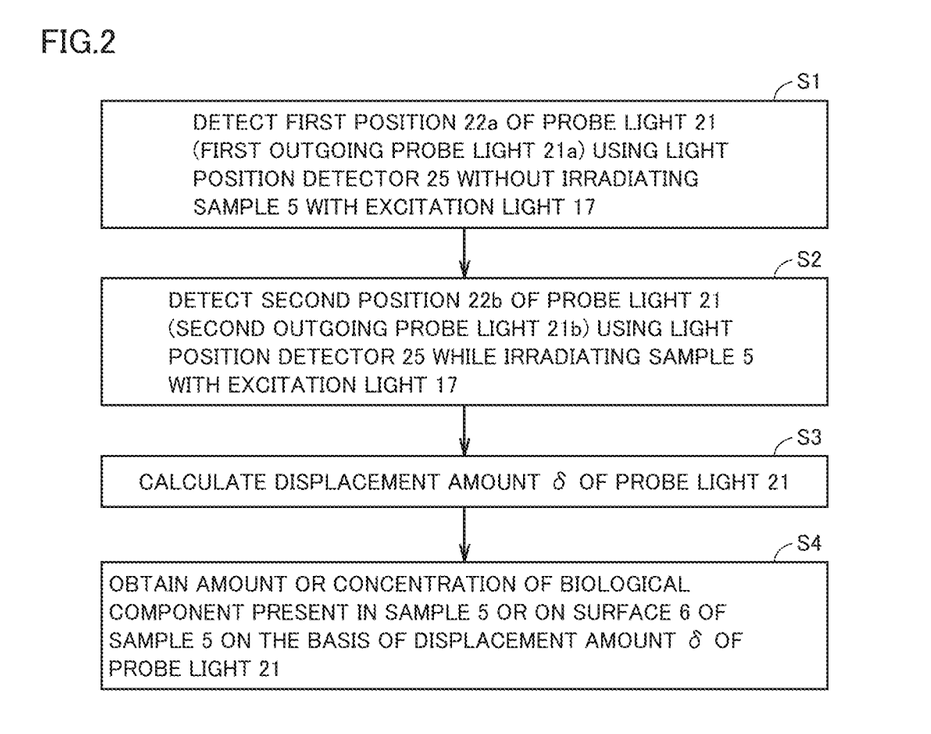
FIG. 2 is a flowchart of a biological component measurement method according to the first embodiment.

With reference to FIG. 2, a biological component measurement method according to the present embodiment using biological component measurement apparatus 1 will be described.

The biological component measurement method according to the present embodiment includes detecting first position 22a of probe light 21 (first outgoing probe light 21a) using light position detector 25 without irradiating sample 5 with excitation light 17 (S1). Since sample 5 is not irradiated with excitation light 17, no absorption heat is generated in sample 5. No temperature gradient region is generated in optical medium 10, and no refractive index gradient region 18 is generated in optical medium 10 accordingly. When sample 5 is not irradiated with excitation light 17, probe light 21 (first outgoing probe light 21a) outgoes from optical medium 10. First position 22a of probe light 21 (first outgoing probe light 21a) is a position of probe light 21 (first outgoing probe light 21a) detected by light position detector 25.

The biological component measurement method according to the present embodiment includes detecting second position 22b of probe light 21 (second outgoing probe light 21b) using light position detector 25 while irradiating sample 5 with excitation light 17 (S2). Since sample 5 is irradiated with excitation light 17, excitation light 17 is absorbed by the biological component present in sample 5 or on surface 6 of sample 5. Excitation light 17 is absorbed by the biological component to generate absorption heat in sample 5. The absorption heat of sample 5 transfers to optical medium 10. The temperature gradient region is generated in optical medium 10, and refractive index gradient region 18 is generated in optical medium 10 accordingly. Probe light 21 is refracted by refractive index gradient region 18, and the traveling direction of probe light 21 changes accordingly. When sample 5 is irradiated with excitation light 17, probe light 21 (second outgoing probe light 21b) outgoes from optical medium 10. Second position 22b of probe light 21 (second outgoing probe light 21b) is a position of probe light 21 (second outgoing probe light 21b) detected by light position detector 25. Irradiating sample 5 with excitation light 17 causes the position of probe light 21 detected by light position detector 25 to shift from first position 22a to second position 22b.

The biological component measurement method according to the present embodiment includes calculating displacement amount δ of probe light 21 (S3). Specifically, biological component acquisition unit 27 calculates the distance between first position 22a and second position 22b to obtain displacement amount δ of probe light 21.

The biological component measurement method according to the present embodiment includes obtaining the amount or concentration of the biological component present in sample 5 or on surface 6 of sample 5 based on displacement amount δ of probe light 21 (S4). For example, biological component acquisition unit 27 is connected to a memory (not illustrated). The memory stores a data table where the type of the biological component, displacement amount δ of probe light 21, and the amount or concentration of the biological component are associated with each other. Biological component acquisition unit 27 consults the data table to obtain the amount or concentration of the biological component associated with the type of the biological component and displacement amount δ of probe light 21.

Figure 3:
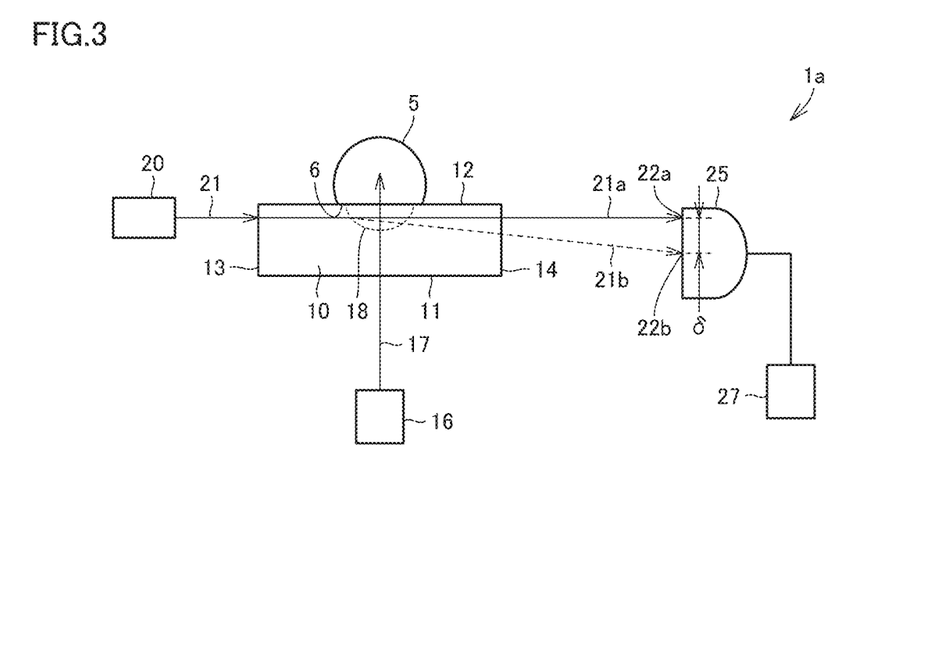
FIG. 3 is a diagram schematically illustrating a biological component measurement apparatus according to a modification of the first embodiment.

With reference to FIG. 3, a biological component measurement apparatus 1a according to a first modification of the present embodiment will be described. According to the first modification of the present embodiment, the normal direction of third surface 13 of optical medium 10 is parallel to the incident direction of probe light 21. Fourth surface 14 is parallel to third surface 13. Probe light 21 travels along the sample placement surface (second surface 12) without being totally internally reflected at the sample placement surface (second surface 12). A biological component measurement method using biological component measurement apparatus 1a is the same as the biological component measurement method using biological component measurement apparatus 1. According to a second modification of the present embodiment, probe light 21 may be totally internally reflected at the interface between the sample placement surface (second surface 12) and sample 5 a plurality of times.

Effects of biological component measurement apparatus 1, 1a according to the present embodiment will be described.

Biological component measurement apparatus 1, 1a according to the present embodiment includes optical medium 10, excitation light source 16, probe light source 20, and light position detector 25. Optical medium 10 includes the sample placement surface (second surface 12). Excitation light source 16 emits, toward sample 5 placed on the sample placement surface (second surface 12), excitation light 17 that travels through optical medium 10. Probe light source 20 emits probe light 21 that travels through optical medium 10. Light position detector 25 detects the position of probe light 21 outgoing from optical medium 10. In plan view of the sample placement surface (second surface 12), an optical path of probe light 21 in optical medium 10 overlaps a part of the sample placement surface (second surface 12) irradiated with excitation light 17. Optical medium 10 is formed from chalcogenide glass.

The chalcogenide glass has a thermal conductivity lower than the thermal conductivity (27.2 W/(m·K)) of zinc sulfide (ZnS). Therefore, the transfer of the absorption heat of sample 5 makes a change in refractive index of refractive index gradient region 18 formed in optical medium 10 larger. This enables biological component measurement apparatus 1, 1a according to the present embodiment to measure the biological component with improved accuracy.

In biological component measurement apparatus 1, 1a according to the present embodiment, the wavelength of probe light 21 is greater than or equal to 1300 nm and less than or equal to 1700 nm. This makes it possible to reduce the risk of damage to human eyes caused by probe light 21. Further, an inexpensive semiconductor laser for use in optical communication may be used as probe light source 20, so that it is possible to reduce the cost of biological component measurement apparatus 1, 1a.

In biological component measurement apparatus 1 according to the present embodiment, probe light 21 is totally internally reflected at the sample placement surface (second surface 12). This allows an increase in distance by which probe light 21 travels through refractive index gradient region 18. This enables biological component measurement apparatus 1 according to the present embodiment to measure the biological component with improved accuracy.

In biological component measurement apparatus 1a according to the present embodiment, probe light 21 travels along the sample placement surface (second surface 12) without being totally internally reflected at the sample placement surface (second surface 12). This enables biological component measurement apparatus 1a according to the present embodiment to measure the biological component with improved accuracy.

Biological component measurement apparatus 1, 1a according to the present embodiment further includes biological component acquisition unit 27 connected to light position detector 25. Light position detector 25 outputs, to biological component acquisition unit 27, first position 22a of probe light 21 (first outgoing probe light 21a) when sample 5 is not irradiated with excitation light 17 and second position 22b of probe light 21 (second outgoing probe light 21b) when sample 5 is irradiated with excitation light 17. Biological component acquisition unit 27 calculates displacement amount δ of probe light 21, which is a distance between first position 22a and second position 22b to obtain the amount or concentration of the biological component present in sample 5 or on surface 6 of sample 5 based on displacement amount δ of probe light 21. This enables biological component measurement apparatus 1, 1a according to the present embodiment to measure the biological component with improved accuracy.

Biological component measurement apparatus 1, 1a according to the present embodiment includes optical medium 10, excitation light source 16, probe light source 20, and light position detector 25. Optical medium 10 includes the sample placement surface (second surface 12). Excitation light source 16 emits, toward sample 5 placed on the sample placement surface (second surface 12), excitation light 17 that travels through optical medium 10. Probe light source 20 emits probe light 21 that travels through optical medium 10. Light position detector 25 detects the position of probe light 21 outgoing from optical medium 10. In plan view of the sample placement surface (second surface 12), an optical path of probe light 21 in optical medium 10 overlaps a part of the sample placement surface (second surface 12) irradiated with excitation light 17. Optical medium 10 is formed from a material having a thermal conductivity of less than or equal to 15.0 W/(m·K).

Therefore, the thermal conductivity of the material of optical medium 10 is less than the thermal conductivity (27.2 W/(m·K)) of zinc sulfide (ZnS). The transfer of the absorption heat of sample 5 makes a change in refractive index of refractive index gradient region 18 formed in optical medium 10 larger. This enables biological component measurement apparatus 1, 1a according to the present embodiment to measure the biological component with improved accuracy.

In biological component measurement apparatus 1, 1a according to the present embodiment, the thermal conductivity of the material of optical medium 10 is less than or equal to 1.0 W/(m·K). Therefore, the thermal conductivity of the material of optical medium 10 is less than the thermal conductivity (27.2 W/(m·K)) of zinc sulfide (ZnS). The transfer of the absorption heat of sample 5 makes a change in refractive index of refractive index gradient region 18 formed in optical medium 10 larger. This enables biological component measurement apparatus 1, 1a according to the present embodiment to measure the biological component with improved accuracy.

In biological component measurement apparatus 1, 1a according to the present embodiment, the thermal conductivity of the material of optical medium 10 is greater than or equal to 0.5 times the thermal conductivity of sample 5. This prevents most of the absorption heat generated in sample 5 from dissipating in the sample 5 and causes this absorption heat to transfer to optical medium 10. This enables biological component measurement apparatus 1, 1a according to the present embodiment to measure the biological component with improved accuracy.

Second Embodiment

Figure 4:
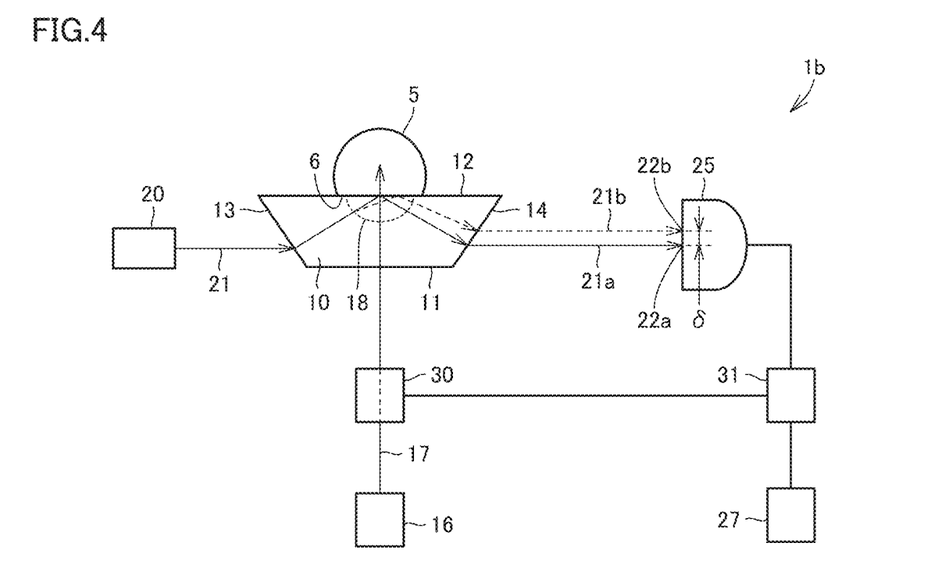
FIG. 4 is a diagram schematically illustrating a biological component measurement apparatus according to a second embodiment.

With reference to FIG. 4, a biological component measurement apparatus 1b according to a second embodiment will be described. Biological component measurement apparatus 1b according to the present embodiment is similar in configuration to biological component measurement apparatus 1 according to the first embodiment, but is different mainly in the following points.

Biological component measurement apparatus 1b further includes an optical chopper 30 and a lock-in amplifier 31. Optical chopper 30 is disposed in the optical path of excitation light 17. Optical chopper 30 interrupts excitation light 17 at a desired frequency. Lock-in amplifier 31 is connected to optical chopper 30 and light position detector 25. Lock-in amplifier 31 selectively amplifies a signal synchronized with the chopping frequency of optical chopper 30 among signals related to the position of probe light 21 output from light position detector 25. This makes it possible to remove noise contained in the signal related to the position of probe light 21 output from light position detector 25. This enables biological component measurement apparatus 1b to measure the biological component with improved accuracy.

Third Embodiment

Figure 5:
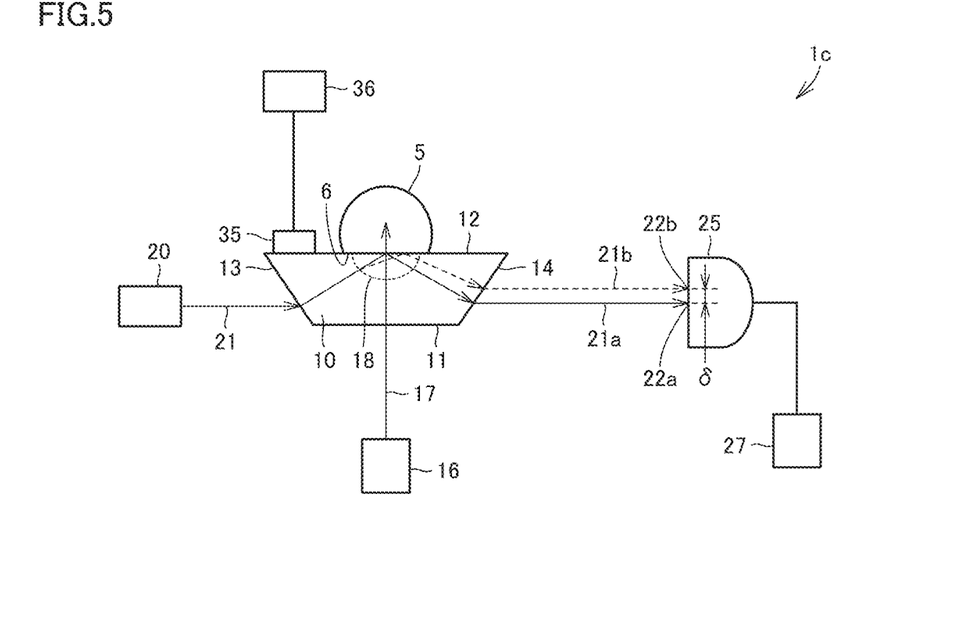
FIG. 5 is a diagram schematically illustrating a biological component measurement apparatus according to a third embodiment.

With reference to FIG. 5, a biological component measurement apparatus 1c according to a third embodiment will be described. Biological component measurement apparatus 1c according to the present embodiment is similar in configuration to biological component measurement apparatus 1 according to the first embodiment, but is different mainly in the following points.

Biological component measurement apparatus 1c further includes a temperature sensor 35. Biological component measurement apparatus 1c may further include a display 36. Temperature sensor 35 is attached to, for example, a portion of optical medium 10 away from sample 5, excitation light 17, and probe light 21. Specifically, temperature sensor 35 is attached to a portion of the sample placement surface (second surface 12) of optical medium 10 away from sample 5, excitation light 17, and probe light 21. Temperature sensor 35 measures the temperature of optical medium 10. Temperature sensor 35 outputs, to display 36, a first signal related to the temperature of optical medium 10. Temperature sensor 35 is, for example, a thermistor. Display 36 displays the temperature of optical medium 10 or a fluctuation range of the temperature of optical medium 10 per unit time. Display 36 is, for example, a liquid crystal display device or the like.

When there is a difference between a first temperature of optical medium 10 and a second temperature of sample 5, heat transfers between optical medium 10 and sample 5. This heat transfer affects refractive index gradient region 18 generated in optical medium 10, making it difficult to accurately measure the biological component. Since optical medium 10 is formed from a material having a low thermal conductivity such as chalcogenide glass, it takes longer for transition from a state (thermal non-equilibrium state) where the fluctuation range of the first temperature of optical medium 10 per unit time is larger than an allowable temperature fluctuation range (for example, 0.1° C./min) to a state (thermal non-equilibrium state) where the fluctuation range of the first temperature of optical medium 10 per unit time is smaller than or equal to the allowable temperature fluctuation range (for example, 0.1° C./min).

Biological component measurement apparatus 1c can obtain the fluctuation range of the first temperature of optical medium 10 per unit time, that is, a degree of heat transfer between optical medium 10 and sample 5, using temperature sensor 35. While the fluctuation range of the first temperature of optical medium 10 per unit time measured by temperature sensor 35 is larger than the allowable temperature fluctuation range (for example, 0.1° C./min) (thermal non-equilibrium state) after sample 5 is placed on the sample placement surface (second surface 12) of optical medium 10, the measurement of the biological component using biological component measurement apparatus 1c is not performed. When the fluctuation range of the first temperature of optical medium 10 per unit time becomes smaller than or equal to the allowable temperature fluctuation range (for example, 0.1° C./min) (thermal non-equilibrium state) after sample 5 is placed on the sample placement surface (second surface 12) of optical medium 10, the measurement of the biological component using biological component measurement apparatus 1c is started.

Biological component measurement apparatus 1c according to the present embodiment further produces the following effects in addition to the effects produced by biological component measurement apparatus 1 according to the first embodiment.

Biological component measurement apparatus 1c according to the present embodiment further includes temperature sensor 35 that measures the temperature of optical medium 10. This allows temperature sensor 35 to measure fluctuations in temperature of optical medium 10 caused by heat transfer between optical medium 10 and sample 5. Even when optical medium 10 is formed from a material having a low thermal conductivity such as chalcogenide glass, it is possible to accurately determine timing at which the measurement of the biological component can be performed without an adverse effect caused by heat transfer between optical medium 10 and sample 5. This enables biological component measurement apparatus 1c according to the present embodiment to measure the biological component with improved accuracy.

Fourth Embodiment

Figure 6:
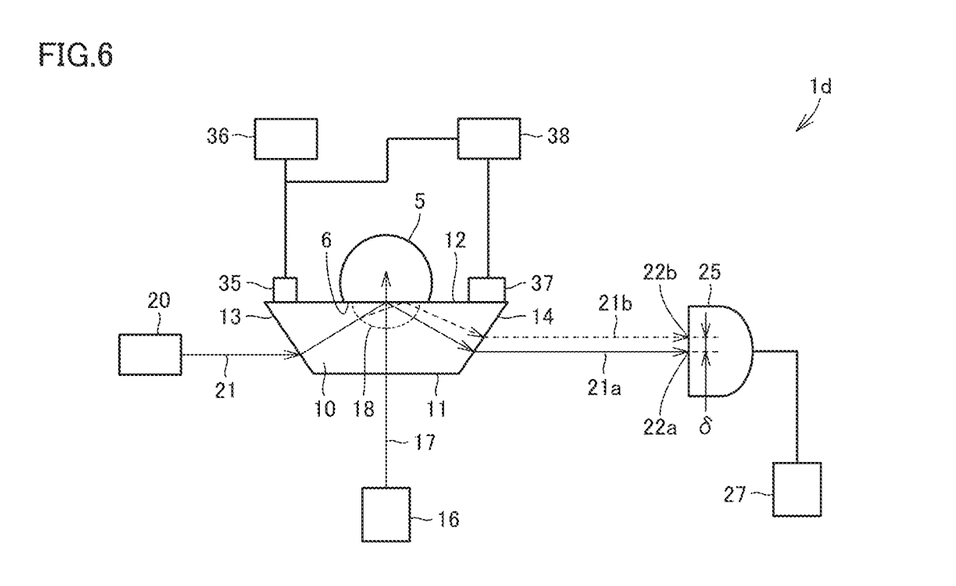
FIG. 6 is a diagram schematically illustrating a biological component measurement apparatus according to a fourth embodiment.

With reference to FIG. 6, a biological component measurement apparatus 1d according to a fourth embodiment will be described. Biological component measurement apparatus 1d according to the present embodiment is similar in configuration to biological component measurement apparatus 1c according to the third embodiment, but is different mainly in the following points.

Biological component measurement apparatus 1d further includes a temperature regulator 37 and a temperature controller 38. Temperature regulator 37 is attached to, for example, a portion of optical medium 10 away from sample 5, excitation light 17, and probe light 21. Specifically, temperature regulator 37 is attached to a portion of the sample placement surface (second surface 12) of optical medium 10 away from sample 5, excitation light 17, and probe light 21. Temperature regulator 37 regulates the temperature of optical medium 10. Temperature regulator 37 is, for example, a Peltier device or an electric heating wire.

Temperature sensor 35 further outputs, to temperature controller 38, the first signal related to the temperature of optical medium 10.

Temperature controller 38 is connected to temperature sensor 35 and temperature regulator 37. Temperature controller 38 controls temperature regulator 37 based on the first signal related to the temperature of optical medium 10 output from temperature sensor 35. Specifically, temperature regulator 37 is controlled to make the fluctuation range of the first temperature of optical medium 10 per unit time measured by temperature sensor 35 smaller or equal to the allowable temperature fluctuation range (for example, 0.1° C./min). For example, when the first temperature of optical medium 10 is lower than the second temperature of sample 5, and the fluctuation range of the first temperature of optical medium 10 per unit time is larger than the allowable temperature fluctuation range, temperature controller 38 controls temperature regulator 37 to cause temperature regulator 37 to heat optical medium 10. When the first temperature of optical medium 10 is higher than the second temperature of sample 5, and the fluctuation range of the first temperature of optical medium 10 per unit time is larger than the allowable temperature fluctuation range, temperature controller 38 controls temperature regulator 37 to cause temperature regulator 37 to cool optical medium 10.

Biological component measurement apparatus 1d according to the present embodiment further produces the following effects in addition to the effects produced by biological component measurement apparatus 1c according to the third embodiment.

Biological component measurement apparatus 1d according to the present embodiment further includes temperature regulator 37 that regulates the temperature of optical medium 10 and temperature controller 38. Temperature controller 38 controls temperature regulator 37 based on the first signal related to the temperature of optical medium 10 output from temperature sensor 35. This makes it possible to reduce, even when optical medium 10 is formed from a material having a low thermal conductivity such as chalcogenide glass, a time taken from the placement of sample 5 on the sample placement surface (second surface 12) of optical medium 10 until heat transfer between optical medium 10 and sample 5 is substantially eliminated to allow the measurement of the biological component to be performed. This enables biological component measurement apparatus 1d to measure the biological component with improved accuracy and in a shorter time.

Fifth Embodiment

Figure 7:
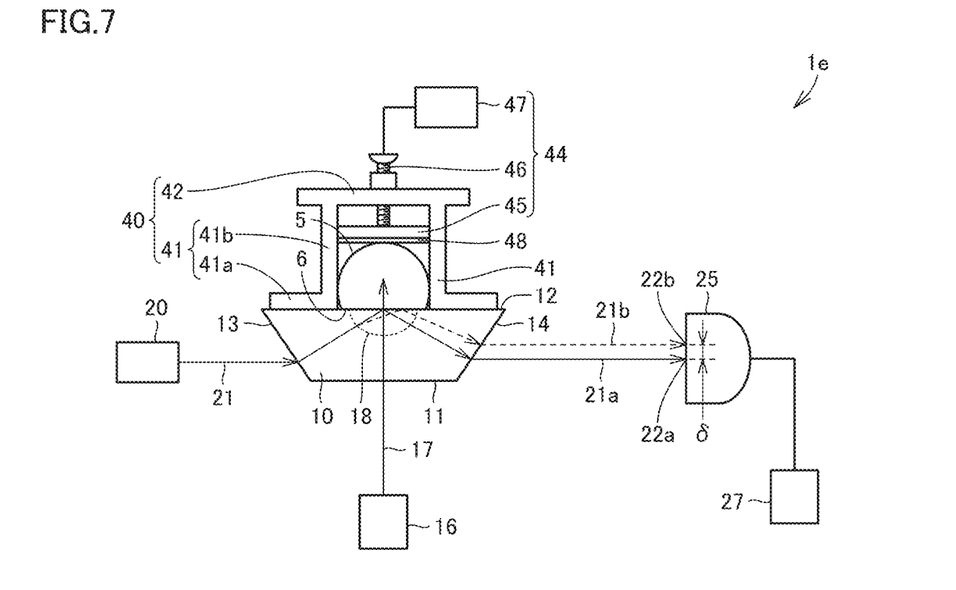
FIG. 7 is a diagram schematically illustrating a biological component measurement apparatus according to a fifth embodiment.
Figure 8:
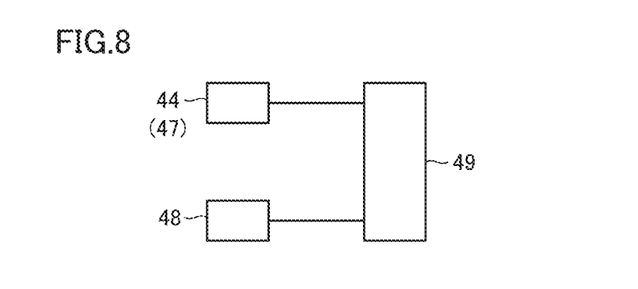
FIG. 8 is a control block diagram of a pressing unit of the biological component measurement apparatus according to the fifth embodiment.

With reference to FIGS. 7 and 8, a biological component measurement apparatus 1e according to a fifth embodiment will be described. Biological component measurement apparatus 1e according to the present embodiment is similar in configuration to biological component measurement apparatus 1 according to the first embodiment, but is different mainly in the following points.

Biological component measurement apparatus 1e further includes a positioning member 40 that defines the position of sample 5 in the traveling direction (left-right direction of FIG. 7) of probe light 21. Positioning member 40 includes a pair of clamping members 41 and a connecting member 42 that connects the pair of clamping members 41. Each of the pair of clamping members 41 includes a bottom plate 41a and a wall 41b extending from bottom plate 41a in the normal direction of the sample placement surface (second surface 12). Bottom plate 41a is in surface-contact with the sample placement surface (second surface 12). Wall 41b is in contact with a side surface of sample 5. The pair of walls 41b of the pair of clamping members 41 clamp sample 5 in the traveling direction of probe light 21.

Biological component measurement apparatus 1e further includes a pressing unit 44, a pressure sensor 48, and a pressure controller 49. Pressing unit 44 presses sample 5 against the sample placement surface (second surface 12). Pressing unit 44 includes, for example, a pressing plate 45, a ball screw 46 that moves pressing plate 45 in the normal direction of the sample placement surface (second surface 12), and a motor 47 that rotates ball screw 46. According to a modification of the present embodiment, pressing plate 45 may be pushed toward sample 5 by an elastic member such as a spring.

Pressure sensor 48 is provided on pressing unit 44. Specifically, pressure sensor 48 is provided on pressing plate 45. Pressure sensor 48 measures pressure with which pressing unit 44 presses sample 5. Pressure sensor 48 outputs, to pressure controller 49, a second signal related to the pressure with which pressing unit 44 presses sample 5. Pressure sensor 48 is, for example, a gauge pressure sensor or a capacitive pressure sensor.

As illustrated in FIG. 8, pressure controller 49 is connected to pressing unit 44 (for example, motor 47) and pressure sensor 48. Pressure controller 49 controls pressing unit 44 based on the second signal related to the pressure output from pressure sensor 48. Specifically, pressing unit 44 (motor 47) is controlled to make the pressure applied to sample 5 and measured by pressure sensor 48 equal to reference pressure. Specifically, when the pressure applied to sample 5 is lower than the reference pressure, pressure controller 49 moves pressing plate 45 toward the sample placement surface (second surface 12) to make the pressure applied to sample 5 equal to the reference pressure. When the pressure applied to sample 5 is higher than the reference pressure, pressure controller 49 moves pressing plate 45 away from the sample placement surface (second surface 12) to make the pressure applied to sample 5 equal to the reference pressure.

Biological component measurement apparatus 1e according to the present embodiment further produces the following effects in addition to the effects produced by biological component measurement apparatus 1 according to the first embodiment.

Biological component measurement apparatus 1e according to the present embodiment further includes pressing unit 44, pressure sensor 48, and pressure controller 49. Pressing unit 44 presses sample 5 against the sample placement surface (second surface 12). Pressure sensor 48 measures pressure with which pressing unit 44 presses sample 5. Pressure controller 49 controls pressing unit 44 based on the second signal related to the pressure output from pressure sensor 48. Therefore, contact pressure between sample 5 and optical medium 10 can be made constant. The transfer of the absorption heat of sample 5 to optical medium 10 becomes stable. This enables biological component measurement apparatus 1e to measure the biological component with improved accuracy.

Biological component measurement apparatus 1e according to the present embodiment further includes positioning member 40 that defines the position of sample 5 in the traveling direction of probe light 21. Therefore, even when sample 5 is a movable sample such as a finger of the patient, it is possible to position sample 5 relative to excitation light 17 and probe light 21 in the traveling direction of probe light 21. This enables biological component measurement apparatus 1e to measure the biological component with improved accuracy.

Sixth Embodiment

Figure 9:
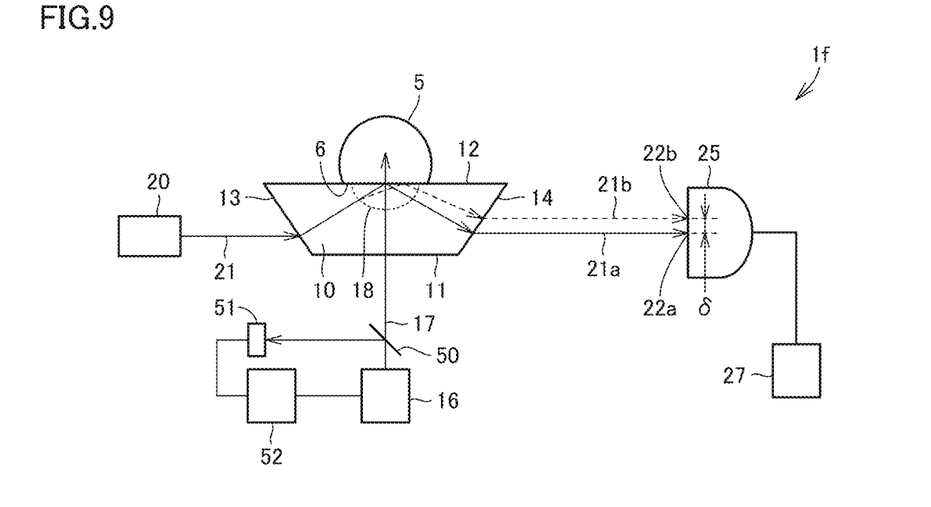
FIG. 9 is a diagram schematically illustrating a biological component measurement apparatus according to a sixth embodiment.

With reference to FIG. 9, a biological component measurement apparatus 1f according to a sixth embodiment will be described. Biological component measurement apparatus 1f according to the present embodiment is similar in configuration to biological component measurement apparatus 1 according to the first embodiment, but is different mainly in the following points. Biological component measurement apparatus 1f further includes a light intensity detector 51 and a light source controller 52. Biological component measurement apparatus 1f may further include a light beam splitter 50.

Light intensity detector 51 detects the intensity of excitation light 17 emitted from excitation light source 16. Light intensity detector 51 is, for example, a photodiode. Specifically, light beam splitter 50 is disposed in the optical path of excitation light 17. Light beam splitter 50 is, for example, a plate light beam splitter, a prism light beam splitter, or an optical fiber light beam splitter. Light beam splitter 50 causes part of excitation light 17 to travel toward light intensity detector 51. Specifically, light beam splitter 50 reflects the part of excitation light 17 toward light intensity detector 51. Light intensity detector 51 detects the light intensity of the part of excitation light 17. Light intensity detector 51 outputs a signal related to the intensity of excitation light 17.

Light source controller 52 is connected to excitation light source 16. Light source controller 52 controls excitation light source 16. Specifically, light source controller 52 controls a current fed to excitation light source 16 to control the intensity of excitation light 17 emitted from excitation light source 16. Light source controller 52 is connected to light intensity detector 51. Light source controller 52 receives the signal related to the intensity of excitation light 17 from light intensity detector 51. Light source controller 52 controls excitation light source 16 based on the signal related to the intensity of excitation light 17 detected by light intensity detector 51 to make the intensity of excitation light 17 emitted from excitation light source 16 constant.

Biological component measurement apparatus 1f according to the present embodiment further produces the following effects in addition to the effects produced by biological component measurement apparatus 1 according to the first embodiment.

Biological component measurement apparatus 1f according to the present embodiment further includes light intensity detector 51 that detects the light intensity of excitation light 17, and light source controller 52 that controls excitation light source 16 based on the signal related to the intensity of excitation light 17 output from light intensity detector 51.

With excitation light source 16 kept in operation for a long time, the light intensity of excitation light 17 emitted from excitation light source 16 may decrease. A decrease in the light intensity of excitation light 17 makes the accuracy of the measurement of the biological component lower. According to the present embodiment, light source controller 52 controls excitation light source 16 based on the signal related to the intensity of excitation light 17 output from light intensity detector 51. This allows the light intensity of excitation light 17 emitted from excitation light source 16 to be maintained over a long period of time. This enables biological component measurement apparatus 1f to measure the biological component with improved accuracy over a long period of time.

It should be understood that the first to sixth embodiments disclosed herein are illustrative in all respects and not restrictive. At least two of the first to sixth embodiments disclosed herein may be combined as long as there is no inconsistency. For example, the second to fifth embodiments may be combined with the modification of the first embodiment. The sixth embodiment may be combined with each of the second to fifth embodiments. The scope of the present disclosure is defined by the claims rather than the above description and is intended to include the claims, equivalents of the claims, and all modifications within the scope.

REFERENCE SIGNS LIST 1, 1a, 1b, 1c, 1d, 1e, 1f: biological component measurement apparatus, 5: sample, 6: surface, 10: optical medium, 11: first surface, 12: second surface, 13: third surface, 14: fourth surface, 16: excitation light source, 17: excitation light, 18: refractive index gradient region, 20: probe light, 21: probe light source, 21a: first outgoing probe light, 21b: second outgoing probe light, 22a: first position, 22b: second position, 25: light position detector, 27: biological component acquisition unit, 30: optical chopper, 31: lock-in amplifier, 35: temperature sensor, 36: display, 37: temperature regulator, 38: temperature controller, 40: positioning member, 41: clamping member, 41a: bottom plate, 41b: wall, 42: connecting member, 44: pressing unit, 45: pressing plate, 46: ball screw, 47: motor, 48: pressure sensor, 49: pressure controller, 50: light beam splitter, 51: light intensity detector, 52: light source controller

The invention claimed is:

1. A biological component measurement apparatus for measuring a component using heat generation of a biological sample absorbing excitation light, the biological component measurement apparatus comprising:
   an optical medium including a biological sample placement surface on which the biological sample is placeable, the optical medium being transparent to the excitation light and being formed from chalcogenide glass that has a lower thermal conductivity than zinc sulfide, and a refractive index of the optical medium being changed by the heat generation of the biological sample absorbing the excitation light;
   an excitation light source to emit, toward the biological sample placement surface, the excitation light that travels through the optical medium;
   a probe light source to emit probe light that travels through the optical medium;
   a light position detector to detect a position of the probe light outgoing from the optical medium; and
   a temperature sensor to measure a temperature of the optical medium, wherein
   the optical medium is also transparent to the probe light,
   the light position detector detects a first position of the probe light outgoing from the optical medium under a first condition where the excitation light source does not emit the excitation light,
   the light position detector detects a second position of the probe light outgoing from the optical medium in which a refractive index gradient region is generated by the heat generation caused by the excitation light under a second condition where the excitation light source emits the excitation light, the component is measured based on the first position and the second position, the temperature sensor is attached to a portion of the biological sample placement surface, the portion being away from the biological sample, the excitation light, and the probe light, and with the biological sample on the biological sample placement surface, the biological component measurement apparatus is operative to prevent the measuring of the component under a first condition where a fluctuation range of temperature of the optical medium per unit time as measured by the temperature sensor is outside of a predetermined allowable temperature fluctuation range, and allow the measuring of the component under a second condition where the fluctuation range of temperature of the optical medium per unit time as measured by the temperature sensor is within the predetermined allowable temperature fluctuation range.

2. The biological component measurement apparatus according to claim 1, wherein
the probe light has a wavelength greater than or equal to 1300 nm and less than or equal to 1700 nm.

3. The biological component measurement apparatus according to claim 1, further comprising:
an optical chopper in an optical path of the excitation light; and
a lock-in amplifier connected to the optical chopper and the light position detector.

4. The biological component measurement apparatus according to claim 1, further comprising:
a temperature regulator to regulate the temperature of the optical medium; and
a temperature controller to control the temperature regulator based on a first signal related to the temperature of the optical medium output from the temperature sensor.

5. The biological component measurement apparatus according to claim 1, further comprising:
a presser including a pressing surface to press the biological sample against the biological sample placement surface;
a pressure sensor to measure pressure with which the presser presses the biological sample; and
a pressure controller to control the presser based on a second signal related to the pressure output from the pressure sensor.

6. The biological component measurement apparatus according to claim 1, further comprising a positioner to define a position of the biological sample in a traveling direction of the probe light.

7. The biological component measurement apparatus according to claim 1, wherein
the probe light is totally internally reflected at the biological sample placement surface.

8. The biological component measurement apparatus according to claim 1, wherein
the probe light travels along the biological sample placement surface without being totally internally reflected at the biological sample placement surface.

9. The biological component measurement apparatus according to claim 1, further comprising a biological component acquirer connected to the light position detector, wherein
the light position detector outputs, to the biological component acquirer, the first position and the second position, and
the biological component acquirer calculates a displacement amount of the probe light that is a distance between the first position and the second position and obtains an amount or concentration of the component present in the biological sample or on a surface of the biological sample based on the displacement amount.

10. The biological component measurement apparatus according to claim 1, wherein
the probe light output from the probe light source is not visible to a human eye and has a first wavelength less than a second wavelength of the excitation light output from the excitation light source.

11. The biological component measurement apparatus according to claim 1, wherein
the optical medium is a total internal reflection (TIR) prism.

12. The biological component measurement apparatus according to claim 1, wherein
the probe light outgoing from the optical medium under the first condition where the excitation light source does not emit the excitation light is received at the light position detector orthogonal to a receiving surface of the light position detector, and
the probe light outgoing from the optical medium under the second condition where the excitation light source emits the excitation light is received at the light position detector orthogonal to the receiving surface of the light position detector.

* * * * *